US006835351B2

(12) United States Patent
Huber et al.

(10) Patent No.: US 6,835,351 B2
(45) Date of Patent: *Dec. 28, 2004

(54) OPTICAL-CHEMICAL SENSOR

(75) Inventors: Christian Huber, Abensberg (DE); Tobias Werner, Regensburg (DE); Otto S. Wolfbeis, Regensburg (DE); Douglas E. Bell, Coral Springs, FL (US); Susannah Young, Norcross, GA (US)

(73) Assignee: F. Hoffmann-La Roche AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/335,843

(22) Filed: Jan. 2, 2003

(65) Prior Publication Data

US 2003/0101803 A1 Jun. 5, 2003

Related U.S. Application Data

(62) Division of application No. 09/900,624, filed on Jul. 6, 2001, which is a continuation of application No. PCT/AT00/00004, filed on Jan. 12, 2000.

(30) Foreign Application Priority Data

Jan. 12, 1999 (AT) .................................................. 37/99

(51) Int. Cl.[7] .............................................. G01N 31/00
(52) U.S. Cl. ...................... 422/82.07; 422/52; 422/55; 422/68.1; 422/82.05; 422/82.06; 422/82.08; 422/82.11
(58) Field of Search .......................... 422/82.07, 82.11; 436/125

(56) References Cited

U.S. PATENT DOCUMENTS

| 4,331,783 A | 5/1982 | Stoy | 525/294 |
|---|---|---|---|
| 4,379,874 A | 4/1983 | Stoy | 524/27 |
| 5,691,205 A | 11/1997 | Kawabata et al. | 436/125 |
| 2002/0034826 A1 * | 3/2002 | Huber et al. | 436/125 |

FOREIGN PATENT DOCUMENTS

| AT | 384 891 B | 1/1988 |
|---|---|---|
| EP | 0358991 B2 | 2/1998 |

OTHER PUBLICATIONS

Jiwan and Soumillion, 1997, "A halogen anion sensor based on the hydrophobic entrapment of a flourescent probe in silica sol–gel films," J. Non–crystalline Solids 220: 316–322.

Martin and Narayanaswamy, 1997, "Studies on quenching of fluorescence of reagents in aqueous solution leading to an optical chloride–ion sensor," Sensors and Actuators B38–39: 330–333.

(List continued on next page.)

Primary Examiner—Yelens Gakh
Assistant Examiner—Sam P. Siefke
(74) Attorney, Agent, or Firm—Roche Diagnostics Operations, Inc.

(57) ABSTRACT

An optical-chemical sensor which is suitable for the continuous and discontinuous determination by luminescence optics of the concentration of chloride in an aqueous sample and which comprises a luminescence indicator (I) and a polymer (H) carrying the luminescence indicator (I) is characterized in that the luminescence indicator (I) is a non-lipophile acridine or bisacridine compound and the polymer (H) is a linear-chain hydrophile polymer soluble in an organic solvent, whereby it is possible to excite the sensor by commercially available LEDs, to manufacture very large numbers thereof at a moderate cost and in a reproducible way and, preferably, to use it for the determination of physiological chloride concentrations and the sensor furthermore has a wide dynamic measuring range for the determination of chloride; a high sensitivity, stability and reproducibility; a high selectivity for chloride; and a low pH cross-sensitivity.

21 Claims, 9 Drawing Sheets

OTHER PUBLICATIONS

Biwersi, Tulk and Verkman, 1994, "Long-wavelength chloride-sensitive fluorescent indicators," Analytical Biochemistry 219: 139–143.

Richard P. Haughland, "Handbook of Fluorescent Probes and Research Chemicals," 6th Edition, pp. 577–579.

V.A. Stoy, "New Type of Hydrogel for Controlled Drug Delivery," J Biomaterials Applications 3, pp. 552–604 (1989).

M.J.P. Leiner and P. Hartmann, "Sensors and Actuators B 11," (1993), pp. 281–289 "Theory and Practice in Optical pH Sensing".

M.J.P. Leiner in Sensors and Actuators B29, (1995), pp. 169–173 ("Optical Sensor for In–Vitro Blood Gas Analysis").

* cited by examiner-

MAC

NPBA

SPBA

AEBA

Lucigenine

FIG. 2
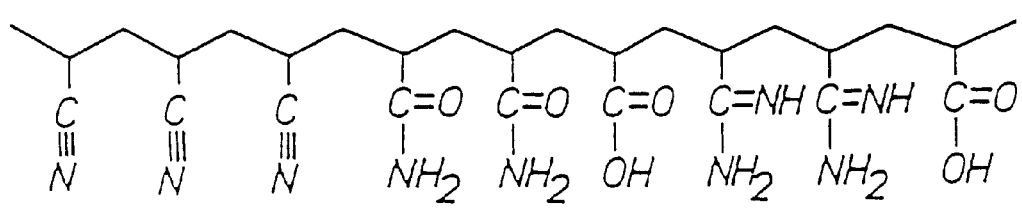
FIG. 2a
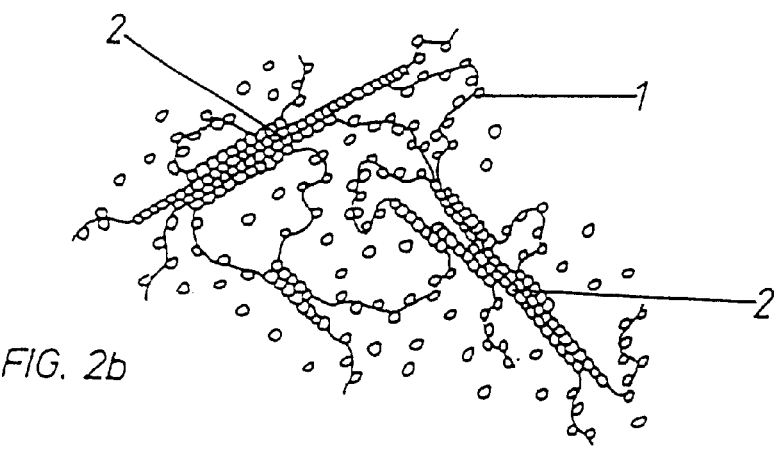
FIG. 2b

US 6,835,351 B2

OPTICAL-CHEMICAL SENSOR

This is a divisional application of U.S. patent application Ser. No. 09/900,624 filed on Jul. 6, 2001 which is a continuation of copending application Serial No. PCT/AT00/00004 filed Jan. 12, 2000, which is incorporated by reference herein, PCT/AT00/00004 was not published in English.

FIELD OF THE INVENTION

The invention relates to an optical-chemical sensor which is suitable for the continuous and discontinuous determination by luminescence optics of the concentration of chloride in an aqueous sample and which comprises a luminescence indicator and a polymer carrying the luminescence indicator, as well as to a process for the production of such an optical-chemical sensor.

BACKGROUND OF THE INVENTION

Chloride is the mainly anionic substance of extracellular liquids in the body and plays an important role in maintaining the distribution equilibrium of water, the osmotic pressure and the equilibrium of anionic and cationic constituents. The normal values of chloride in the human blood serum are approximately 97–108 mmol/l; the total concentration of anionic substances is approximately 154 mmol/l. Pathological chloride values—of up to 170 mmol/l—are found in the case of osmotic diuresis plus insufficient water supply, when the mechanism of the thirst regulation is disturbed, in the case of nephrogenic diabetes insipidus and in the case of enteral bicarbonate losses. Minimum values— of down to 30 mmol/l—are found in the case of gastrointestinal chloride losses and are associated with the chronic pyelonephritis (Addison's disease) and renal failure. Therefore, chloride is the halide which in clinical diagnostics has to be determined most frequently.

Besides titrimetric and photometric determination methods, which are very accurate but also involve much work, potentiometric methods with ion-selective electrodes have become generally accepted in practice. The disadvantages are the minor specificity of chloride-selective electrodes, their sensitivity to proteins and the need for a reference electrode.

Recently, a series of optical sensors having indicator systems partly working in different manners have been proposed for the chloride determination. The so-called coextraction optode (EP 0 358 991) is based on a lipophile pH indicator dye with a lipophile counterion, is very sensitive to lipophile anionic constituents of the sample and only provides useful results when the pH value is very exactly known.

It is known that both the luminescence intensity and the luminescence decay time of certain luminescence indicators are diminished by dynamic luminescence quenching of halide ions. This is expressed by the Stern-Vollmer equation:

$$\frac{F_0}{F} = 1 + k_q \cdot \tau_0 \cdot [Q] = 1 + K_{SV} \cdot [Q]$$

In this equation, $F_0$ and F stand for the relative luminescence intensities in the absence and presence of a quencher, [Q] for the concentration of the quencher, $k_q$ for the bimolecular rate constant for the quenching, $\tau_0$ for the lifetime of the excited state in the absence of a quencher and $K_{SV}$ for the Stern-Vollmer quenching constant. Thus, it is possible to deduce the chloride concentration of the sample from the relative luminescence intensity and/or the luminescence decay time of the luminescence indicator.

A chloride-sensitive optode on the basis of a quinoline or acridine dye which is covalently linked to a glass surface and the luminescence of which is quenched as a function of the halide concentration was proposed in AT-B 384 891.

Chloride-sensitive luminescence indicators having quaternized heteroaromatic N atoms have a low pH crosssensitivity and a low cross-sensitivity to physiological concentrations of disturbing ions. However, when it comes to commercial applications involving very large numbers, the disadvantages are the absorption wavelengths of <450 nm which are in the ultraviolet spectral range (not accessible with blue LEDs that are commercially available at a moderate cost) and the chemical immobilization on the surfaces of suitable transparent carrier materials, which is cumbersome in particular when dealing with large numbers.

For the investigation of the chloride transport and of regulation mechanisms in isolated membrane vesicles, reconstituted liposomes and living cells and tissues by luminescence measuring, a series of quinoline and acridine derivatives and lucigenine (a bisacridine) are commercially available (Richard P. Haughland, "Handbook of Fluorescent Probes and Research Chemicals", $6^{th}$ edition, pp. 577–579).

A chloride-sensitive optical-chemical sensor on the basis of a 3,6-bis(dimethylamino)-acridine being present in a polyacrylamide layer and having a lipophile aliphatic hydrocarbon chain with up to 30 C atoms is described in U.S. Pat. No. 5,691,205. This indicator can be excited by a blue light source (LED) at 488 nm.

The production of this known sensor comprises the production-at the end of a light-conducting fiber-of a thin membrane or layer consisting of polyacrylamide by photopolymerization of a monomer solution consisting of acrylamide-N,N'-methylenebis(acrylamide), riboflavin and ammonium peroxodisulfate. Subsequently, the membrane or layer is immersed into an indicator solution, the lipophile indicator diffusing into the membrane or layer. U.S. Pat. No. 5,691,205 does not give information on stability properties of that sensor, particularly the leaching property of the indicator in the case of a quite long contact with measuring liquids, such as blood.

In the case of the sensor known from U.S. Pat. No. 5,691,205, the disadvantages are, particularly with a view to the production of large numbers of constant quality, the manufacturing step of the membrane or layer by photopolymerization of a monomer solution and the covering of the membrane or layer with an indicator. With regard to a constant quality of the sensors, this step is very cumbersome.

SUMMARY OF THE INVENTION

The present invention has as its object to provide an optical-chemical sensor which is suitable for the determination by luminescence optics of the concentration of chloride in an aqueous sample and which does not have the above-indicated disadvantages. In particular, it should be possible to excite the sensor by commercially available LEDs (excitation wavelength >460 nm), to manufacture very large numbers thereof at a moderate cost and in a reproducible way and, preferably, to use it for the determination of physiological chloride concentrations.

In an optical-chemical sensor which is suitable for the continuous and discontinuous determination by luminescence optics of the concentration of chloride in an aqueous sample and which comprises a luminescence indicator and a polymer carrying the luminescence indicator, the object of the invention is achieved in that the luminescence indicator is a non-lipophile acridine or bisacridine compound and the polymer is a linear-chain hydrophile polymer soluble in an organic solvent. The term of "linear-chain" should express that the polymer is not cross-linked.

It is obvious that the polymer should not be soluble substantially in the sample, e.g. blood, sea water, salt-containing aqueous liquids.

The advantages of such a sensor for measuring chloride are a wide dynamic measuring range, in particular in the physiologically relevant concentration range of chloride;

the high sensitivity;

the high stability and reproducibility;

the high selectivity for chloride; and a low pH cross-sensitivity in the physiologically relevant pH-value range.

Preferably, the acridine or bisacridine compound is selected from a group comprising methylacridinium methosulfate (MAC), 4-nitrophenylbutylacridinium methosulfate (NPBA), N,N'-di-(3-sulfopropyl)-9,9-bisacridinium (SPBA), N,N'-diacetic acid ethyl ester-9,9-bisacridinium (AEBA) and lucigenine.

As polymer, ion-permeable multiple block copolymers containing acid amide and nitrile and/or acid imide and/or carboxylate groups are preferred.

For example, such a linear-chain hydrophile polymer is commercially available multiple block copolymer HYPAN, available from HYMEDIX Int. Inc., Dayton, N.J., which will be mentioned in more detail below. It is decisive that this polymer can be dissolved in an organic solvent such as DMSO, wherein it is likewise easy to evaporate the solvent after the solution has been applied to a transparent carrier material, so that a simple and reproducible production of a sensor is enabled.

Multiple block copolymers that can be used in accordance with the invention are characterized in that each polymer chain consists of several sequences of units having hydrophile properties, e.g. independently of each other acid amide groups which also may be replaced by hydrophile groups, acid imide groups, carboxylate groups and several sequences having groups of high cohesive energy, e.g. nitrile groups. The production of such polymers is described for example in U.S. Pat. No. 4,331,783 and U.S. Pat. No. 4,379,874.

Surprisingly, it has been found that the above-named acridine and bisacridine compounds diffuse into the polymer when the linear-chain hydrophile polymer is immersed into a solution of these compounds and can only be leached slowly afterwards. Thus, the present invention provides a very stable sensor.

Among the above-indicated acridine and bisacridine compounds, lucigenine is particularly suitable for the determination of physiological chloride concentrations in blood, serum and plasma thanks to the following properties:

(a) high quenching constant $K_{SV}$ in solution ($K_{SV}(Cl^-)$ >100 $M^{-1}$);

(b) excitation maximum above 450 nm, so that an inexpensive LED may be used as a light source;

(c) large Stokes shift;

(d) high photostability;

(e) luminescence quantum yield higher than 0.5; and (f) commercial availability.

According to a preferred embodiment of the sensor according to the invention, the polymer carrying the luminescence indicator is applied in the form of a film to a transparent carrier material. Here, the film preferably has a thickness of up to 20 μm. It is essential that the film is not soluble in aqueous liquids, i.e. in the sample or the calibration liquids.

According to another preferred embodiment, the polymer carrying the luminescence indicator is embedded in the form of fine particles in a hydrogel film applied to a transparent carrier material. Here, the size of the particles can be up to 20 μm and preferably is <1 μm. By this particularly advantageous embodiment, large quantities of luminescence-indicator-carrying material can be manufactured in one manufacturing step at a moderate cost. Another essential advantage is that with this material, large quantities of sensors can be produced, which have particularly uniform characteristics, such as characteristic curve and luminescence-indicator load.

Hydrogels used in accordance with the invention are ion-permeable hydrophile polymers insoluble in water or aqueous salt solutions. Preferably, they should be soluble in organic solvents or solvent mixtures (e.g. EtOH/H$_2$O) in which the polymer carrying the luminescence indicator is insoluble, so that the solvent can be evaporated after the application of the layer. Hydrogels preferably used are the linear-chain hydrophile polymers of Tyndale Plains-Hunter (see below), for example. In principle, it is also possible to use other hydrogels, e.g. cross-linked polymers, in particular polyacrylamide, the monomer solution being polymerized after the application.

Preferably, an additional layer is applied to the film or hydrogel film that is on the transparent carrier material, which layer is composed of a hydrophile, ion-permeable polymer and preferably contains color pigments, in particular black pigments. Advantageously, this additional layer brings about an optical uncoupling of the sensor from the measuring medium. It acts as an ion-permeable optical isolating layer.

According to another embodiment, the transparent carrier material is a light-conducting fiber, the film carrying the luminescence indicator being applied to a light-conducting fiber.

The invention also relates to a process for the production of an optical-chemical sensor which is suitable for the continuous and discontinuous determination by luminescence optics of the concentration of chloride in an aqueous sample and which comprises a luminescence indicator and a polymer carrying the luminescence indicator, characterized in that a non-lipophile luminescence indicator on the basis of an acridine or bisacridine compound is used as luminescence indicator and a linear-chain hydrophile polymer soluble in an organic solvent is used as polymer, wherein a solution of the luminescence indicator is produced and the solution is brought into contact with the linear-chain hydrophile polymer, the luminescence indicator diffusing into the linear-chain hydrophile polymer.

According to a preferred embodiment, the luminescence indicator diffused into the linear-chain hydrophile polymer is immobilized by radiation, preferably with ultraviolet and/or blue light (320 nm to 490 nm).

When using a multiple block copolymer of the HYPAN type, it was surprisingly found that particularly acridines and bisacridines having at least one methyl group on the quaternized N atom (e.g. MAC, lucigenine) are not leached after radiation with blue and/or ultraviolet light, even in the case of a quite long contact with measuring liquids. This leaching incapacity is essential particularly in measurements performed in a continuous manner ("monitoring") and in the case of a multiple use of sensors.

Experiments established for example that with HYPAN HN80 radiated with blue or ultraviolet light and carrying MAC (FIG. 1) or lucigenine, the solvent liberated from the polymer was clear and the polymer fraction still had the typical yellow coloring of the indicator after the polymer had been dissolved in DMSO and the solution had been centrifugated under addition of MeOH. A corresponding control experiment with an indicator-carrying polymer not radiated with blue or ultraviolet light established that the solvent liberated from the polymer had the typical yellow coloring of the indicator and the polymer fraction was uncolored. This experiment suggests that the radiation of the indicator-carrying polymer with blue or ultraviolet light leads to a covalent linkage of the indicator to the polymer without adversely influencing the quenching capacity of the indicator luminescence.

Experiments with other polymers containing acid amide groups, e.g. polyacrylamide, established that said indicators can also be introduced into these polymers by a contact with aqueous indicator solutions, whereupon they can be leached slowly. After radiation of the polymer with blue or ultraviolet light, MAC and lucigenine are not leached any more.

A preferred embodiment of the process according to the invention is characterized in that a solution of the linear-chain hydrophile polymer is produced;

the solution is applied to a transparent carrier material and the solvent is allowed to evaporate, a film of the linear-chain hydrophile polymer being formed on the transparent carrier material;

the film is brought into contact with the solution of the luminescence indicator, the luminescence indicator diffusing into the film and optionally being immobilized by radiation.

Preferably, the thickness of the film is up to 20 $\mu$m. By punching small disks out of the coated transparent carrier material, individual sensor elements are produced. In principle, this process step is known from the literature (M. J. P. Leiner, Optical Sensors for in vitro Blood Gas Analysis, Sensors and Actuators B 29, (1995) 169–173).

Another preferred embodiment of the process according to the invention is characterized in that the solution of the luminescence indicator is brought into contact with a powdery linear-chain hydrophile polymer, the luminescence indicator diffusing into the linear-chain hydrophile polymer and optionally being immobilized by radiation;

the linear-chain hydrophile polymer carrying the luminescence indicator is suspended in a hydrogel solution, a suspension being formed;

the suspension is applied to a transparent carrier material; and the solvent is allowed to evaporate from the hydrogel solution, wherein on the transparent carrier material there is formed a hydrogel film in which the linear-chain hydrophile polymer carrying the luminescence indicator is embedded.

Here, the linear-chain hydrophile polymer is preferably used with a particle size of less than 1 $\mu$m. However, the particle size may also be up to 20 $\mu$m.

The advantage of this procedure is that using aliquot portions of one and the same charge of the luminescence-indicator-covered powdery linear-chain hydrophile polymer for many sensor production charges allows large quantities of sensors having very uniform properties to be produced.

Then, from the carrier material thus coated, individual sensor elements can be produced by punching small disks.

The invention further relates to a process for the determination of the concentration of chloride in an aqueous sample while using the optical-chemical sensor according to the invention.

BRIEF DESCRIPTION OF THE FIGURES

In the following, the invention will be explained in more detail with reference to the drawings and to exemplary embodiments.

FIG. 2 depicts the structure of a linear-chain hydrophile polymer that is preferably used and is commercially available under the trademark of HYPAN (HYMEDIX Int. Inc., Dayton, N.J.). In this multiple block copolymer, hydrophile sequences form continuous amorphous ion-permeable areas (so-called soft blocks, 1), while cohesive sequences form crystalline clusters (so-called hard blocks, 2). An accurate description of those multiple block copolymers can be found in V. A. Stoy, New Type of Hydrogel for Controlled Drug Delivery, J. Biomedical Applications 3, 553–604 (1989).

FIGS. 3 and 4 each show a disk S of the sensor according to the invention. The chloride-sensitive luminescence indicator immobilized in HYPAN is referred to as I. According to FIG. 3, the HYPAN carrying luminescence indicator I is, in the form of a thin film H, on a carrier material T, transparent for the excitation and emission light. According to FIG. 4, the HYPAN carrying luminescence indicator I is, in the form of suspended particles, in a hydrogel G, which in the form of a thin film is applied to a carrier material T, transparent for the excitation and emission light. For the optical uncoupling of the film carrying luminescence indicator I from measuring medium P, an ion-permeable optical isolating layer O, which consists of a pigmented hydrogel, is applied to film H and/or film G.

The optical measuring means consists of a LED as a light source L, a photodiode M as a detector, optical filters A and F for selecting the wavelengths, an optical arrangement for conducting the excitation light into polymer layer H and/or polymer layer G and for conducting the emission light to photodiode M as well as a means for signal processing (not represented). On the side of the excitation, an interference filter (peak transmission at 480 nm) was used, and on the side of the emission, a 550 nm cut-off filter.

Figure 1:
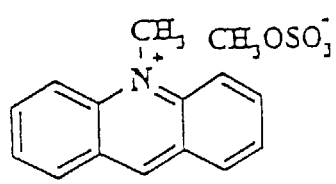
FIG. 1 depicts luminescence indicators that are preferably used. The figure shows the structural formulas of the luminescence indicators of methylacridinium methosulfate (MAC), 4-nitrophenylbutylacridinium methosulfate (NPBA), N,N'-di-(3-sulfopropyl)-9,9-bisacridinium (SPBA), N,N'-diacetic acid ethyl ester-9,9-bisacridinium (AEBA) and lucigenine.
Figure 1:
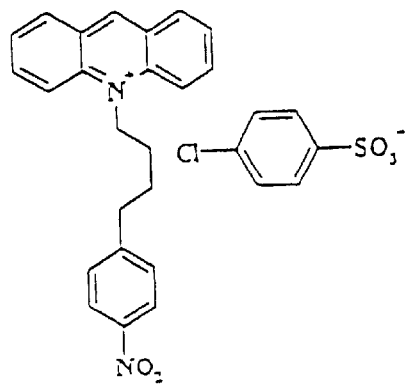
Figure 1:
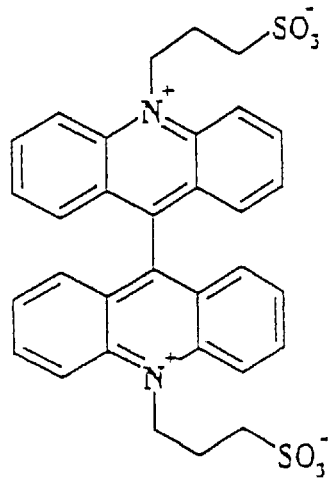
Figure 1:
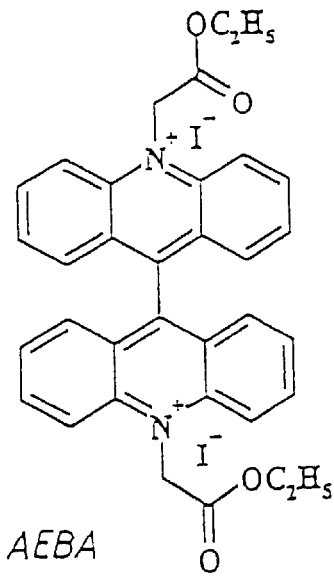
Figure 1:
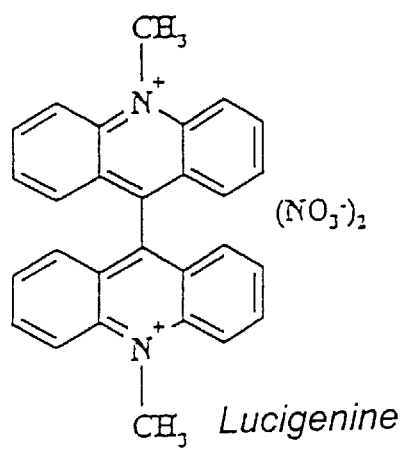
Figure 3:
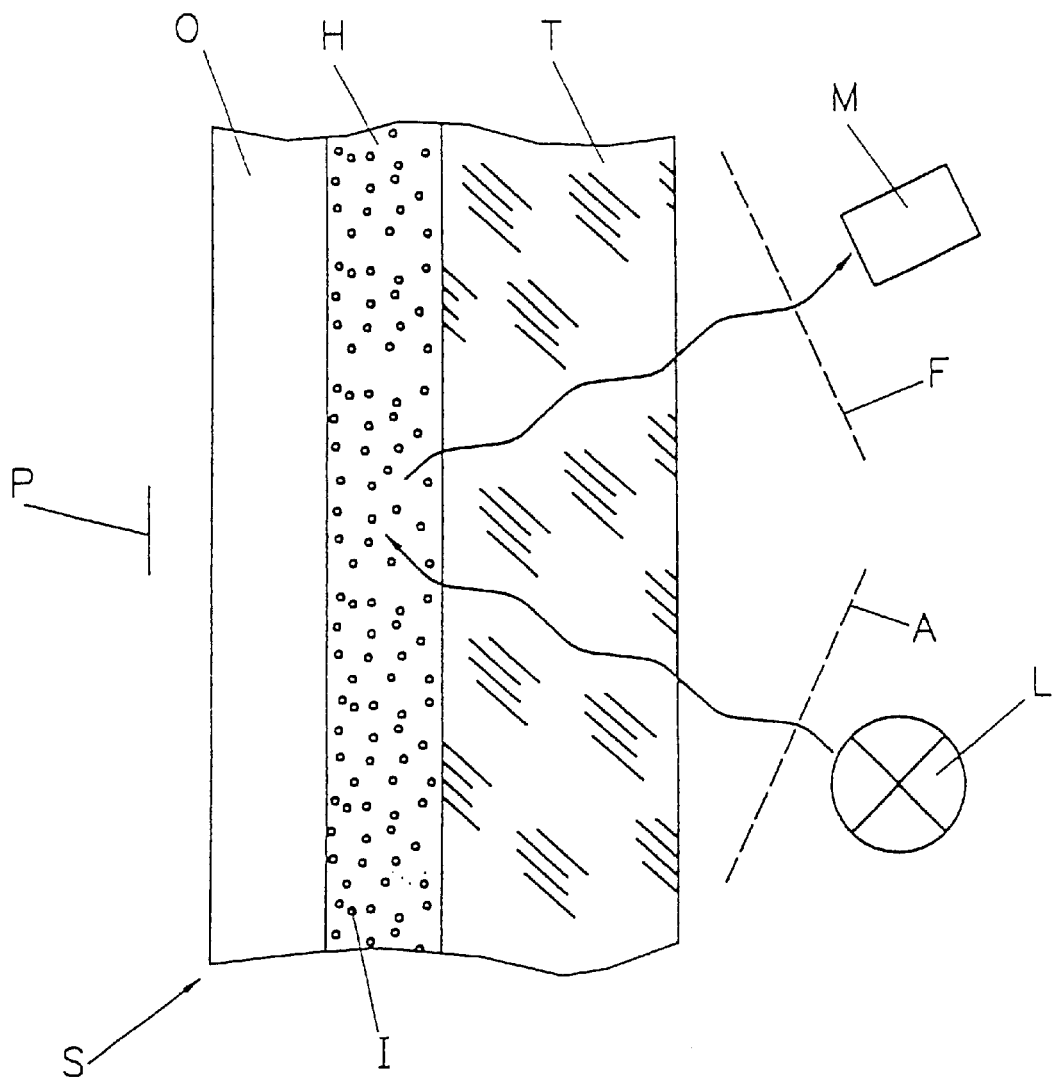
FIG. 3 diagrammatically shows the constitution of an inventive sensor according to a preferred embodiment, the polymer carrying the luminescence indicator being applied in the form of a film to a transparent carrier material.
Figure 5:
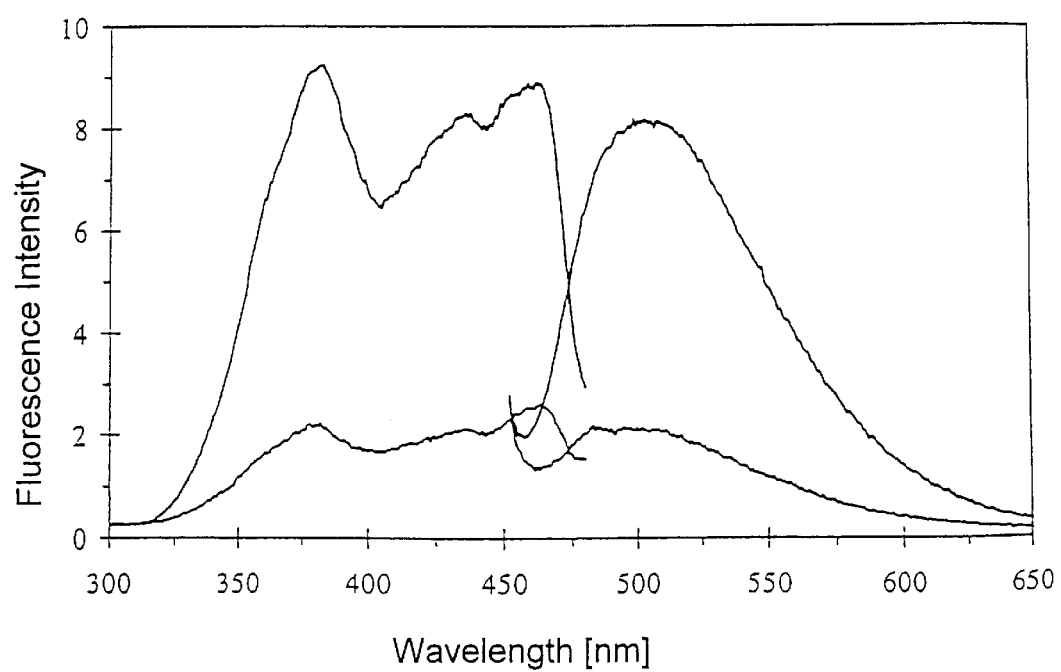

FIG. 5 shows the excitation and emission spectrum of the luminescence indicator of lucigenine, preferably used in the sensor according to the invention, which was recorded with a measuring arrangement according to FIG. 3 while using a commercially available fluorimeter.

Figure 6:
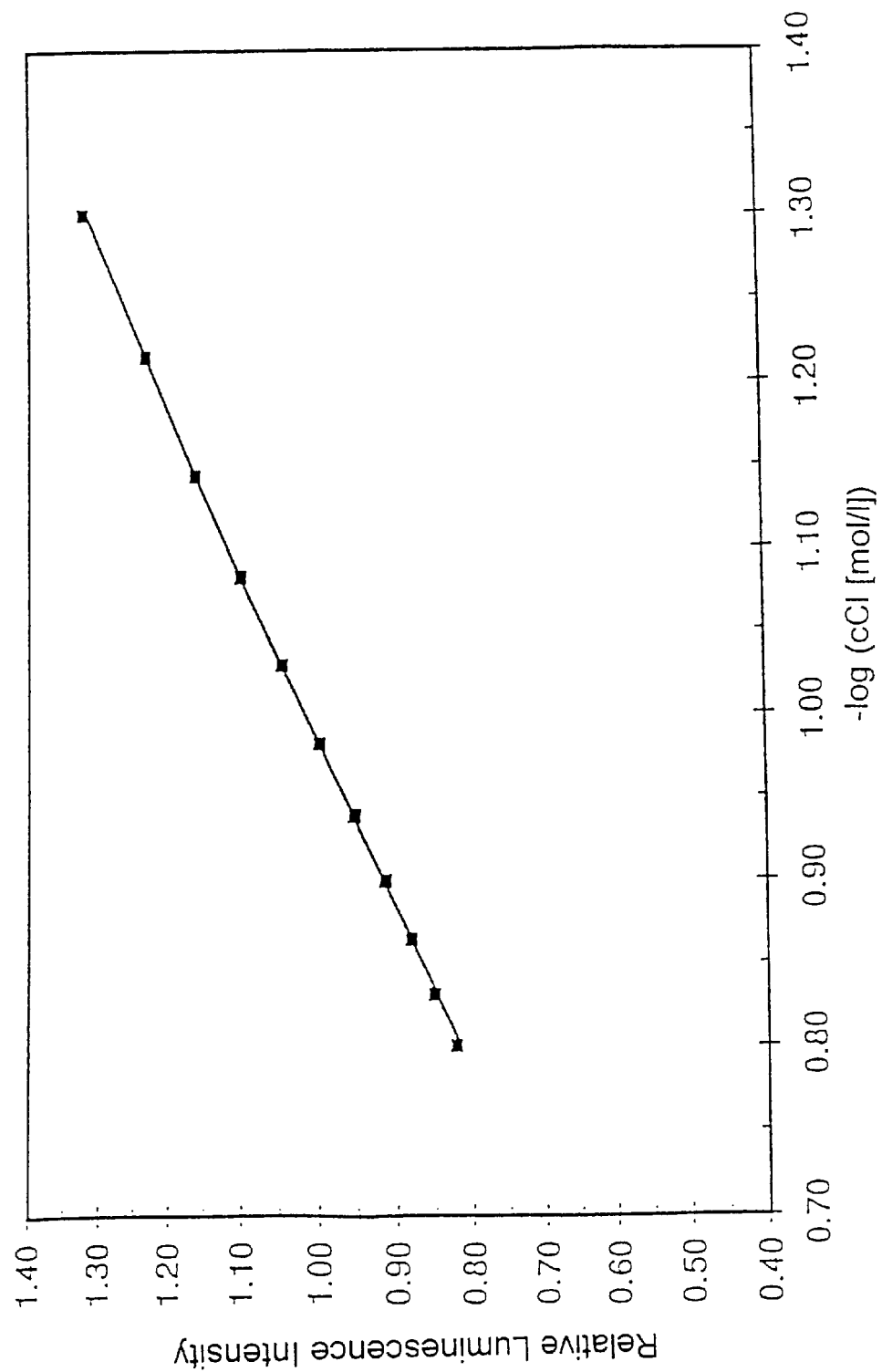

FIG. 6 shows relative luminescence intensities of an inventive sensor according to the constitution scheme of FIG. 3 as a function of the concentration of chloride.

Figure 7:
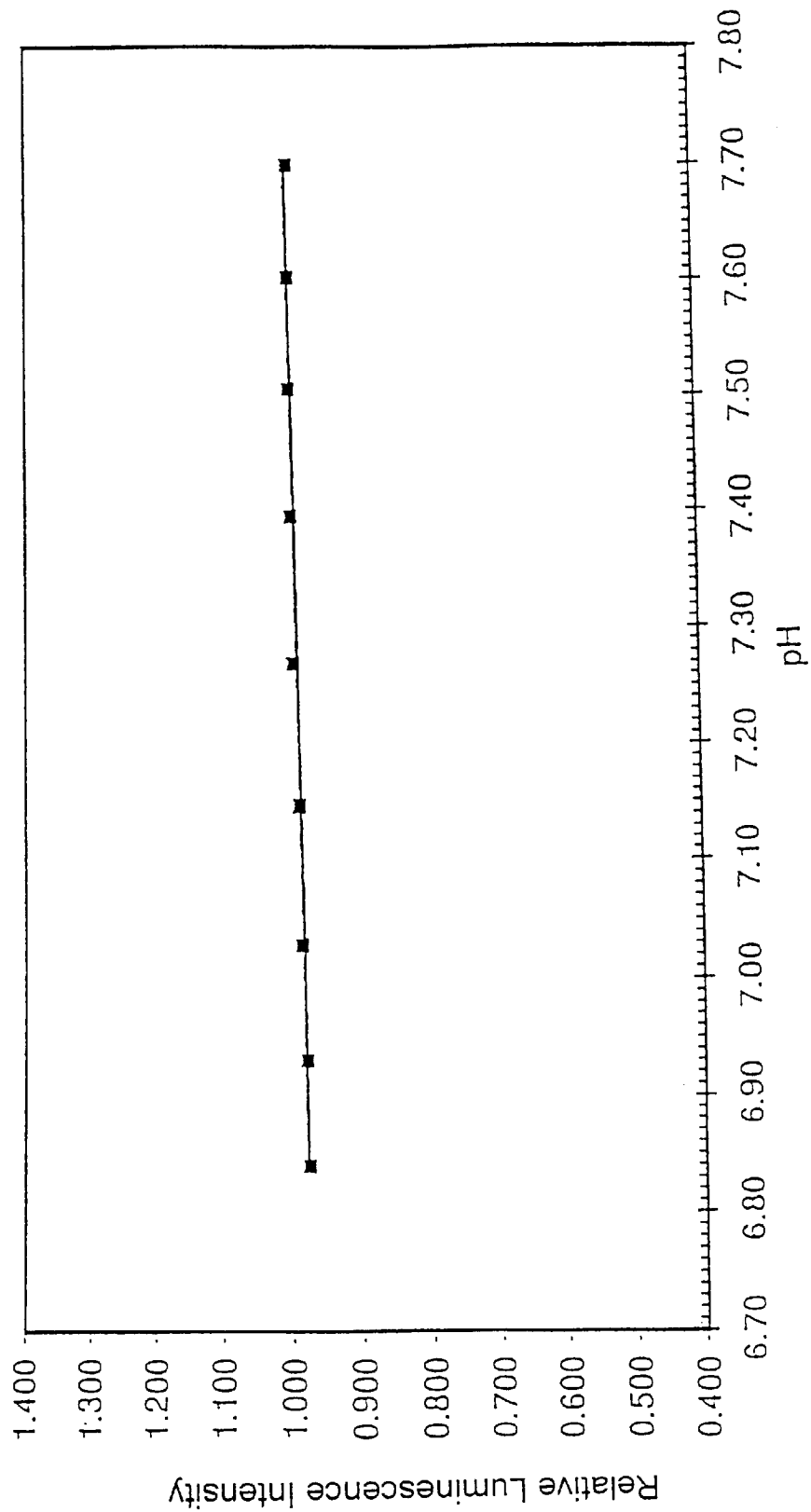

FIG. 7 shows relative luminescence intensities of that sensor as a function of the pH value of the measuring medium.

Figure 4:
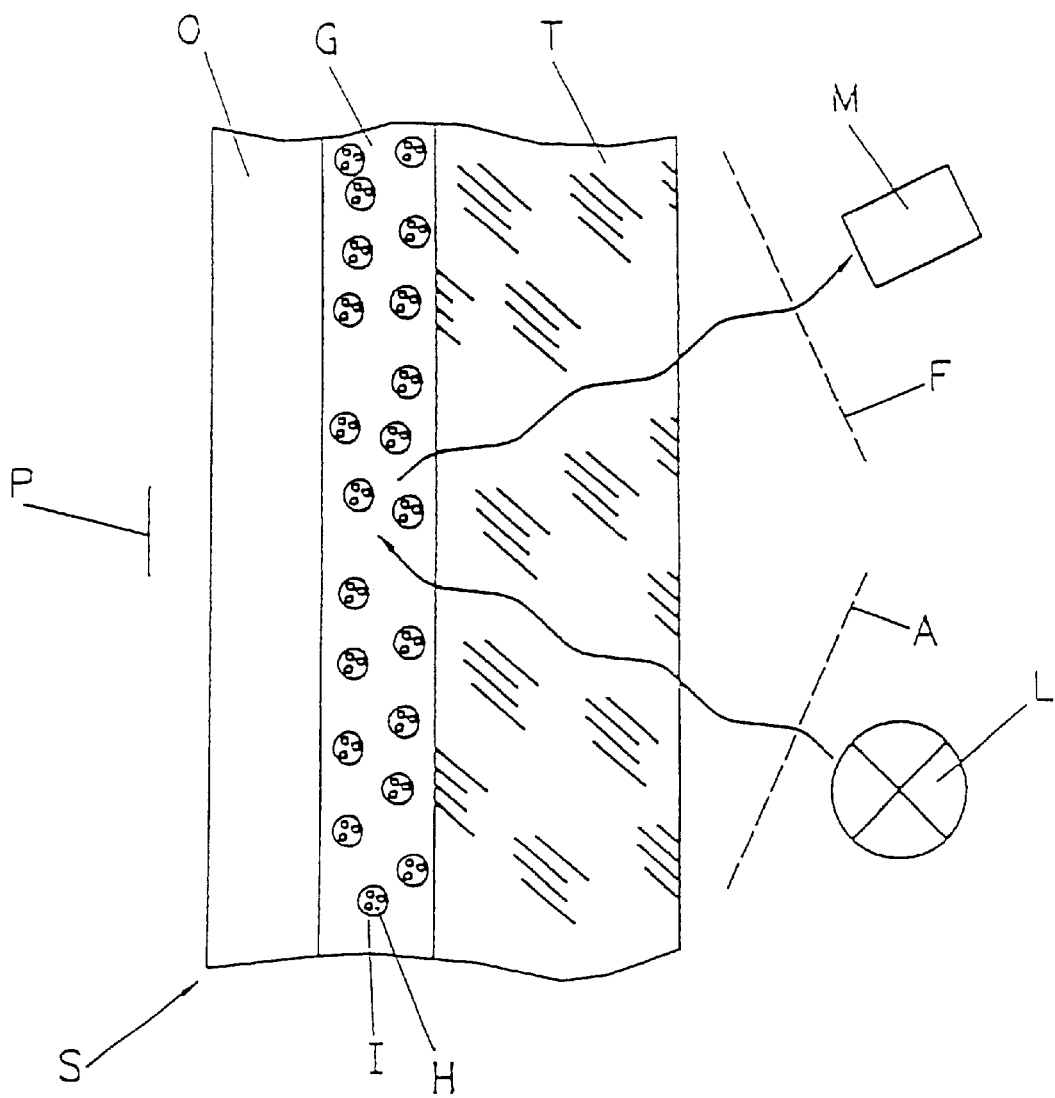
FIG. 4 diagrammatically shows another preferred embodiment of the inventive sensor, the polymer carrying the luminescence indicator being embedded in the form of small particles in a hydrogel film applied to the transparent carrier material.
Figure 8:
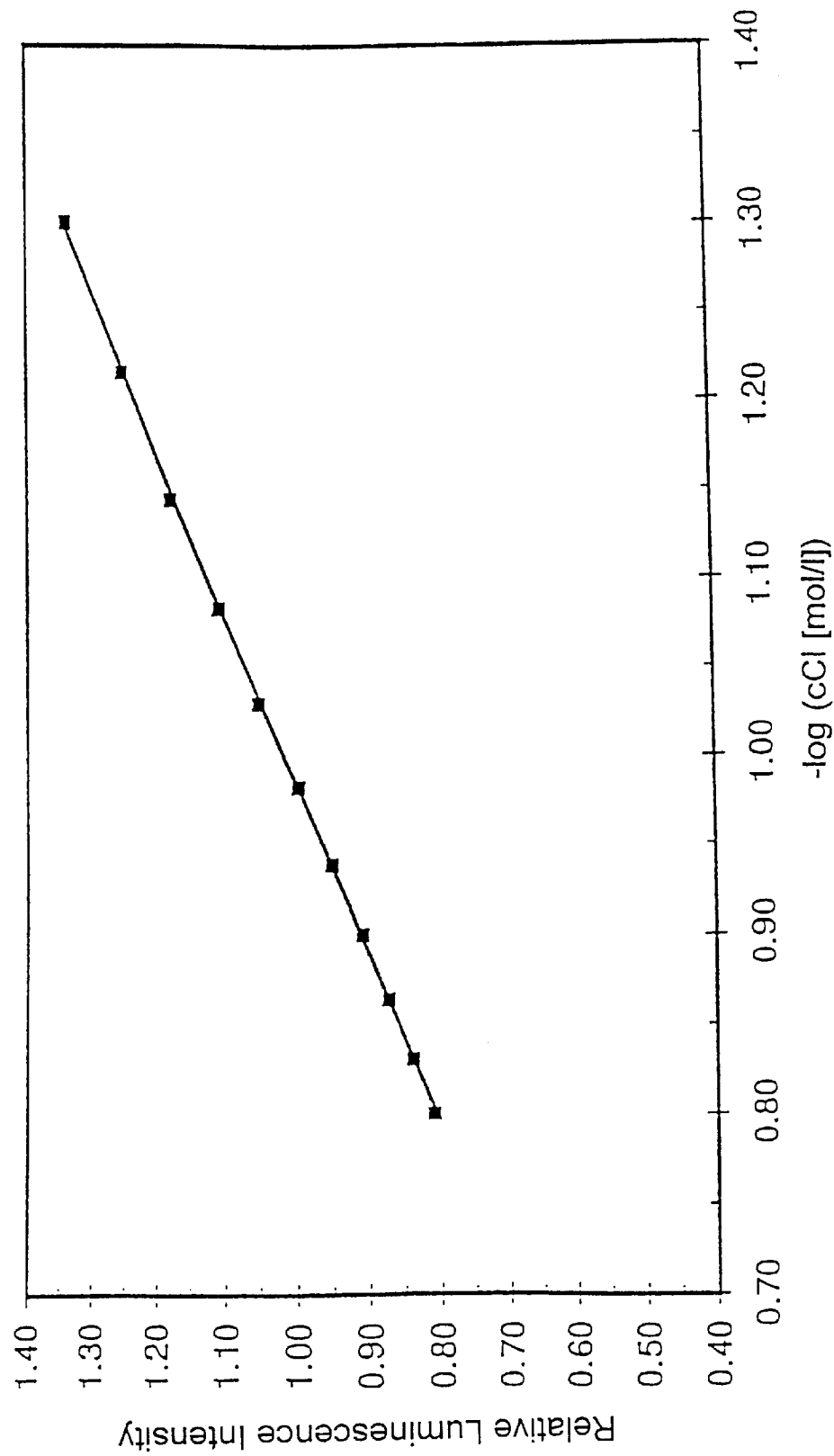
Figure 9:
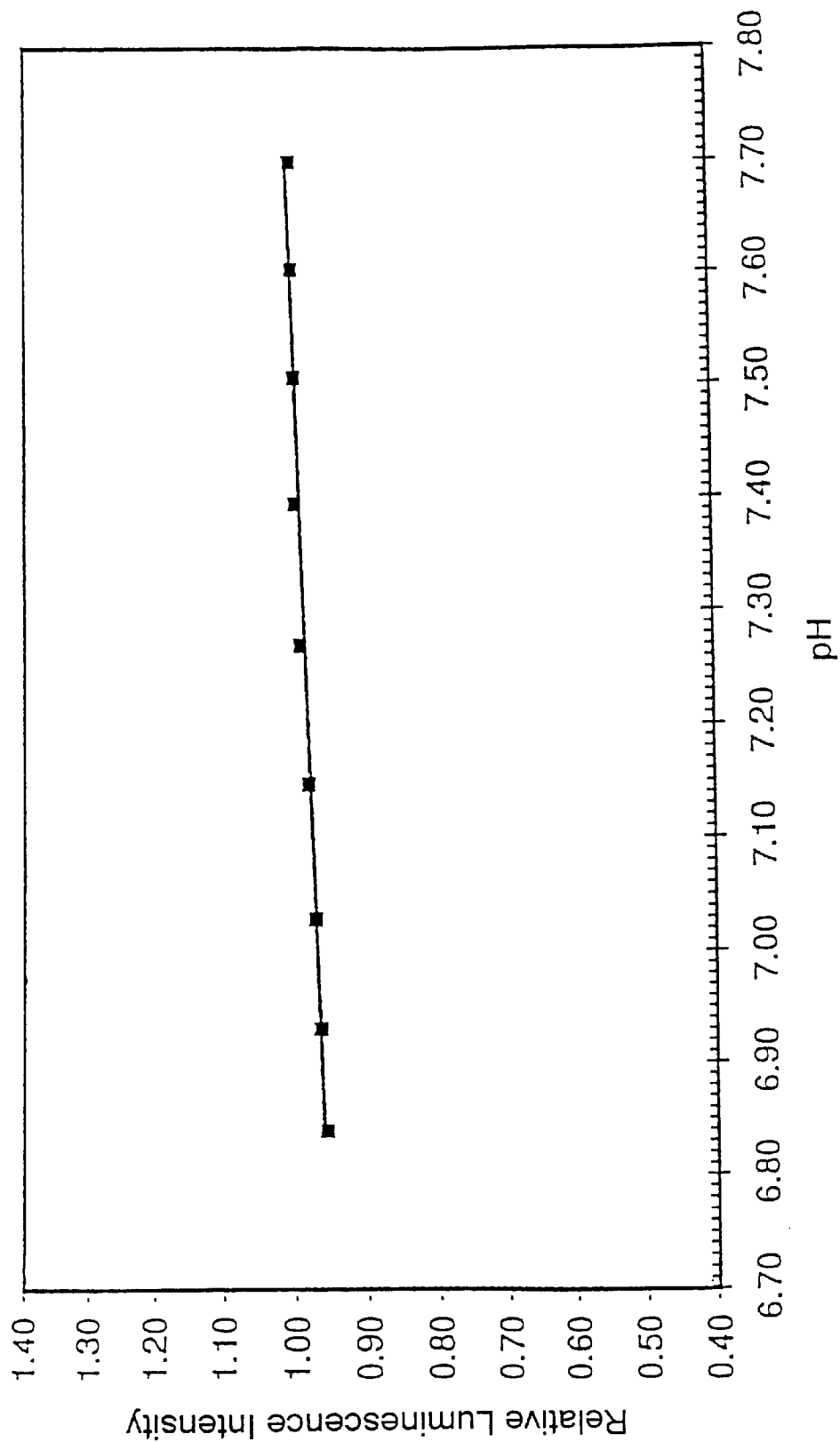

FIGS. 8 and 9 show relative luminescence intensities as a function of the concentration of chloride or as a function of the pH value for an inventive sensor according to the constitution scheme of FIG. 4.

DETAILED DESCRIPTION OF THE INVENTION

EXAMPLE 1 (FIG. 3)

Production of Sensors having a Polymer Film Carrying the Luminescence Indicator

Preparation of Films Coated with HYPAN:

6 g of HYPAN HN80 (HYMEDIX Int. Inc., Dayton, N.J. 08810, USA) by aid of a magnetic stirrer were dissolved in 80 ml of DMSO at 60° C. over five hours. By aid of a knife-edge straight-edge, 4.5 ml of the solution obtained were applied with a wet thickness of 100 $\mu$m to a polyester film (MYLAR, Plastic Suppliers, USA) located on a planar support. For the purpose of evaporating the solvent, the film was retained at room temperature for 20 minutes and subsequently was immersed into deionized water for 30 seconds.

Covering of the HYPAN-Coated Films with the Luminescence Indicator:

A 300 $\mu$M lucigenine solution (Aldrich Chemical Company Inc., # B4920-3, USA) was prepared by dissolving 135 mg of lucigenine in 1 l of deionized water. Thereafter, the HYPAN-coated film in an appropriate vessel was immersed into the lucigenine solution for 1 hour, a portion of the lucigenine diffusing into the HYPAN layer of the film. Then, the HYPAN layer was washed with deionized water.

UV Treatment of the Luminescence-indicator-covered Film:

For the treatment with ultraviolet light, the luminescence-indicator-covered film in an open vessel was put with the HYPAN layer on a 12.7 mm (½ inch) layer of deionized water and subsequently was radiated with a UV lamp from a distance of 10 cm for one hour. Thereafter, for the purpose of rinsing non-linked indicator, the film was immersed for one hour into 250 ml of a 100 mM NaF solution (4.3 g of NaF and 4.13 g of NaH$_2$PO$_4$, dissolved in 900 ml of deionized water, set to pH 7.1 with 5 N NaOH and then filled up to 1 liter with H$_2$O). Afterwards, the luminescence-indicator-covered HYPAN layer was rinsed with deionized water.

Preparation and Application of an Ion-permeable Optical Isolating Layer to the Luminescence-indicator-covered Film:

1.5 g of cellulose fibers sieved through a 25 $\mu$m sieve (VWR Scientific, P.O. Box 669967, Marietta, Ga. 30065, USA; Product No. JT 1528-1) and 3.5 g of Fe$_2$O$_3$ (Fischer Scientific Company, # 1116-3) were suspended for 16 hours in 17 g of a solution consisting of 1.8% by weight hydrogel D6 (Tyndale Plains-Hunter Ltd., Ringoes, N.J. 08551, USA) and 55% by weight ethanol in water. 5 ml of the homogeneous suspension obtained were applied with a wet thickness of 100 $\mu$m to the HYPAN layer, humidified with deionized water and covered with the luminescence indicator, of the UV-treated film. After the evaporation of the solvent at room temperature, disks having a diameter of 2.5 cm were cut out and stored dust-free and dry at room temperature until their use. Before their use, the disks were retained in the buffer for at least 16 hours for activation purposes.

Production of Sensor Disks:

A method for cutting and measuring sensor disks was described by M. J. P. Leiner and P. Hartmann in Sensors and Actuators B 11 (1993), pages 281–289 ("Theory and Practice in Optical pH Sensing") and by M. J. P. Leiner in Sensors and Actuators B 29 (1995), pages 169–173 ("Optical Sensors for in vitro Blood Gas Analysis").

The sensor disks obtained according to that method were used in the measuring arrangement depicted diagrammatically in FIG. 3.

EXAMPLE 2 (FIG. 4)

Production of Sensors from Luminescence-indicator-covered Particles

Preparation of HYPAN Particles:

Powdery HYPAN HN80 (mean grain diameter 130 $\mu$m) was obtained directly from the manufacturer, HYMEDIX. Smaller grain diameters (50 nm–20 $\mu$m) were obtained by fine-grinding the material with a laboratory jet mill (Glen Mills Inc., 395 Altwood Road, Cliftton, N.J. 07012, USA). A fraction with a narrower grain-diameter range (50–500 nm) was obtained by sieving the finely ground material with metal sieves.

Covering the HYPAN Particles with the Luminescence Indicator and Immobilizing the Indicator:

A 300 $\mu$M lucigenine solution was prepared by dissolving 135 mg of lucigenine in 1 l of deionized water and the solution was put into a crystallizing dish with a magnetic stirrer. Then, 50 g of HYPAN HN80 powder were slowly added to the solution while stirring.

A UV lamp (Upland, Calif. 91786, USA, Model XX15, 115V, 60 Hz, 0.68A; emission blue-near UV) was positioned 10 cm above the suspension and the latter was treated with UV light for 4 hours while constantly stirring. Subsequently, the indicator-covered particles were separated from the covering solution by means of a Büchner funnel and using a filtering paper, were put into a further crystallizing dish and then were suspended—while stirring—for 1 hour in 1 liter of a 100 mM NaF solution (4.3 g of NaF and 4.13 g of NaH$_2$PO$_4$, dissolved in 900 ml of deionized water, set to pH 7.1 with 5 N NaOH and then filled up to 1 liter with H$_2$O). The suspension was filtered and the powder was washed with deionized water until the filtrate was colorless. Thereafter, the powder in the Büchner funnel in absolute ethanol was suspended and washed and at room temperature was dried overnight. For the purpose of removing residual agglomerates, the powder was sieved through a 50 $\mu$m metal sieve. Until its further use, the powder was stored in an exsiccator over CaCl$_2$.

Preparation of Luminescence-indicator-coated Films:

By aid of a magnetic stirrer, 1.2 g of the indicator-covered powder, sieved to 50 $\mu$m, in a closed vessel were suspended for 12 hours in 6.8 g of a solution consisting of 1.8% by weight hydrogel D6 (Tyndale Plains-Hunter Ltd., Ringoes, N.J.) and 55% by weight ethanol in water. Then, the homogeneous suspension was applied with a wet thickness of 150 $\mu$m to a polyester film (MELINEX) and the solvent was brought to evaporate overnight at room temperature.

The application of an ion-permeable optical isolating layer and the production of sensor disks were carried out as described in Example 1.

Determination of the Luminescence Properties of the Sensors According to the Invention For the purpose of measuring the luminescence intensity of sensors according to the invention, sensor disks produced in accordance with the above-described process were introduced into a light-permeable thermostatted measuring cell and were brought into contact with samples having different chloride concentrations and different pH values.

FIG. 5 shows the luminescence excitation and emission spectrum of a sensor produced in accordance with Example 1 (without ion-permeable optical isolating layer), at pH 7.1, (A) in contact with a 200 mM NaCl solution and (B) in contact with a 200 mM NaF solution.

FIGS. 6 and 8 show the relative luminescence intensities of sensors according to the invention, produced in accordance with Example 1 and/or Example 2, in contact with aqueous solutions, as a function of the negative common logarithm of the chloride concentration (0.050, 0.061, 0.072, 0.082, 0.093, 0.104, 0.115, 0.125, 0.136, 0.147, 0.159 mol/l).

As measuring media, 0.1M HEPES buffers, $CO_2$-free, pH 7.4 (37° C.), having different concentrations of NaCl, were used.

As is apparent from FIGS. 6 and 8, both differently constituted sensors are suitable for the determination of physiological (blood) concentrations of chloride.

FIGS. 7 and 9 show the relative luminescence intensities of sensors according to the invention, produced in accordance with Example 1 and/or Example 2, in contact with aqueous solutions, as a function of the pH value (6.819, 6.910, 7.009, 7.123, 7.250, 7.363, 7.481, 7.575, 7.671).

As measuring media, 0.1M HEPES buffers having different concentrations of HEPES acid and HEPES Na salt and with a chloride concentration of 0.104 mol/l were used.

As is apparent from FIGS. 7 and 9, the inventive sensors do not exhibit a dependence on the pH value of the measuring medium in the range of physiological pH values. The slight ascent of the pH characteristic curves is due to a weak interaction with the HEPES salt of the exemplary measuring media. Such high concentrations of HEPES salt do not exist in natural measuring media (body fluids, sea water, etc.).

The present invention is not limited to the represented exemplary embodiments. For example, the person skilled in the art in an analogous way may produce sensors by using chloride-sensitive luminescence indicators other than lucigenine, for example by using the above-indicated compounds.

What is claimed is:

1. An optical-chemical sensor which is suitable for the continuous and discontinuous determination by luminescence optics of the concentration of chloride in an aqueous sample and which comprises a luminescence indicator (I) and a polymer (H) carrying the luminescence indicator (I), characterized in that the luminescence indicator (I) is a non-lipophile acridine or bisacridine compound and the polymer (H) is a linear-chain hydrophile polymer soluble in an organic solvent, the luminescence indicator (I) being immobilized in the polymer (H).

2. An optical-chemical sensor according to claim 1, characterized in that the acridine or bisacridine compound is selected from a group comprising methylacridinium methosulfate (MAC), 4-nitrophenylbutylacridinium methosulfate (NPBA), N,N'-di-(3-sulfopropyl)-9,9-bisacridinium (SPBA), N,N'-diacetic acid ethyl ester-9,9-bisacridinium (AEBA) and lucigenine.

3. An optical-chemical sensor according to claim 1 or 2, characterized in that the linear-chain hydrophile polymer is a multiple block copolymer containing acid amide and/or acid imide and/or carboxylate and/or nitrile groups.

4. An optical-chemical sensor according to claim 1 or 2, characterized in that the polymer (H) carrying the luminescence indicator (I) is applied in the form of a film to a transparent carrier material (T).

5. An optical-chemical sensor according to claim 1 or 2, characterized in that the polymer (H) carrying the luminescence indicator (I) is embedded in the form of fine particles in a hydrogel film (G) applied to a transparent carrier material (T).

6. An optical-chemical sensor according to claim 4, characterized in that an additional layer (O) is applied to the film or hydrogel film (G) that is on the transparent carrier material (T), which layer is composed of a hydrophile ion-permeable polymer.

7. An optical-chemical sensor according to claim 4, characterized in that the transparent carrier material (T) is a light-conducting fiber.

8. An optical-chemical sensor according to claim 6 wherein the additional layer (O) contains at least one color pigment.

9. An optical-chemical sensor according to claim 6 wherein the additional layer (O) contains black pigment.

10. An optical-chemical sensor according to claim 3, characterized in that the polymer (H) carrying the luminescence indicator (I) is applied in the form of a film to a transparent carrier material (T).

11. An optical-chemical sensor according to claim 3, characterized in that the polymer (H) carrying the luminescence indicator (I) is embedded in the form of a fine particles in a hydrogel film (G) applied to a transparent carrier material (T).

12. An optical-chemical sensor according to claim 5, characterized in that an additional layer (O) is applied to the film or hydrogel film (G) that is on the transparent carrier material (T), which layer is composed of a hydrophile ion-permeable polymer.

13. An optical-chemical sensor according to claim 5, characterized in that the transparent carrier material (T) is a light-conducting fiber.

14. An optical-chemical sensor according to claim 6, characterized in that the transparent carrier material (T) is a light-conducting fiber.

15. An optical-chemical sensor according to claim 10, characterized in that the transparent carrier material (T) is a light-conducting fiber.

16. An optical-chemical sensor according to claim 11, characterized in that the transparent carrier material (T) is a light-conducting fiber.

17. An optical-chemical sensor according to claim 12, characterized in that the transparent carrier material (T) is a light-conducting fiber.

18. An optical-chemical sensor according to claim 11 wherein the additional layer (O) contains at least one color pigment.

19. An optical-chemical sensor according to claim 11 wherein the additional layer (O) contains black pigment.

20. An optical-chemical sensor according to claim 12 wherein the additional layer (O) contains at least one color pigment.

21. An optical-chemical sensor according to claim 12 wherein the additional layer (O) contains black pigment.

* * * * *